United States Patent [19]

Weis et al.

[11] Patent Number: 4,740,604

[45] Date of Patent: Apr. 26, 1988

[54] BENZANTHRONE LACTONES

[75] Inventors: Claus D. Weis, Pfeffingen; Peter Sutter, Muttenz, both of Switzerland

[73] Assignee: Ciba-Geigy Corporation, Ardsley, N.Y.

[21] Appl. No.: 49,915

[22] Filed: May 15, 1987

[30] Foreign Application Priority Data

May 26, 1986 [CH] Switzerland .................. 2113/86

[51] Int. Cl.$^4$ ............................................. C07D 307/77
[52] U.S. Cl. ..................................... 549/297; 260/376; 260/383; 534/753; 534/765
[58] Field of Search ........................................ 549/297

[56] References Cited

U.S. PATENT DOCUMENTS 1,818,025  12/1927  Wolfram et al. .................. 549/297

Primary Examiner—Jane T. Fan
Attorney, Agent, or Firm—Kevin T. Mansfield; Edward McC. Roberts

[57] ABSTRACT

There are disclosed benzanthrone lactones of formula

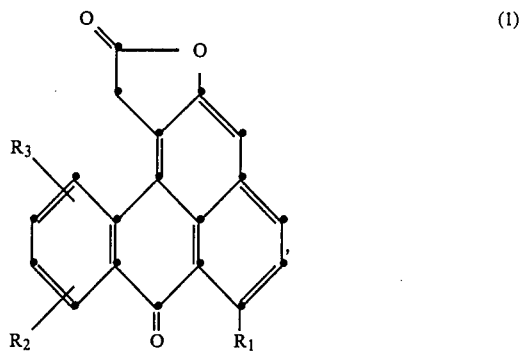

(1)

wherein $R_1$, $R_2$ and $R_3$ are as defined in claim 1.

The benzanthrone lactones of formula (1) are important intermediates for the synthesis of novel dyes which are obtained by coupling suitable diazo components to said compounds of formula (1).

5 Claims, No Drawings

BENZANTHRONE LACTONES

The present invention relates to benzanthrone lactones, to their preparation and to novel dyes which contain them as coupling components.

Benzanthrone and a host of substituted derivatives have long been known as e.g. intermediates for the synthesis of dyes and pigments. So far, however, benzanthrone lactones have not been described.

Novel benzanthrone lactones have now been found which have surprising properties and, in addition, are important intermediates for e.g. the synthesis of dyes.

Accordingly, the present invention relates to benzanthrone lactones of formula

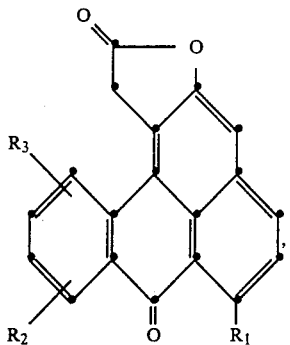
(1)

wherein $R_1$ is hydrogen or hydroxy and $R_2$ and $R_3$ are each independently of the other hydrogen, chlorine, hydroxy, methoxy or benzamido.

The preferred meaning of $R_1$ is hydrogen and $R_2$ and $R_3$, each independently of the other, are preferably hydrogen, chlorine or benzamido, with hydrogen being most preferred.

In a preferred embodiment of the benzanthrone lactones of this invention, $R_1$, $R_2$ and $R_3$ are each hydrogen.

The benzanthrone lactones of the present invention can be prepared e.g. by reacting a 1-anthraquinone diazonium salt of formula

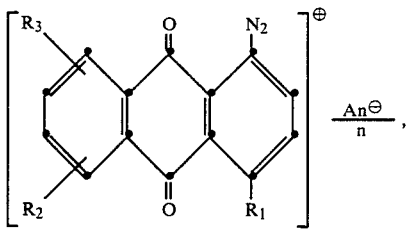
(2)

wherein $R_1$, $R_2$ and $R_3$ are as defined in claim 1, An is an anion and n is the valency of said anion, with 2-methyleneglutaronitrile in the presence of a catalytic amount of a metal of auxiliary group VIII or I, of a salt of said metals or of a mixture of a corresponding salt and metal powder, in an organic solvent, reacting the intermediate so obtained of formula

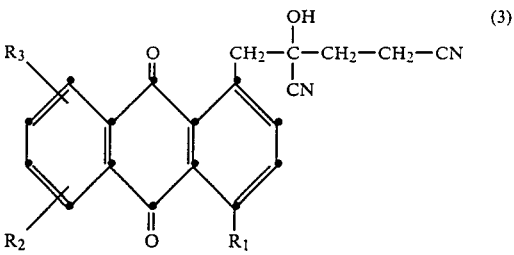
(3)

to the compound of formula

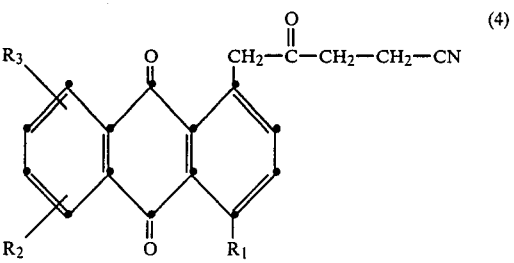
(4)

which is then cyclised, in alkaline medium, to the benzanthrone lactone of formula (1).

The anion An is e.g. a chloride or sulfate ion and n is thus 1 or 2.

The 1-anthraquinone diazonium salt is preferably a 1-anthraquinone diazonium sulfate.

The 1-anthraquinone diazonium salt is preferably in solid form, e.g. in the form of a dry powder or moist paste. It can be obtained in a manner known per se by diazotisation of 1-aminoanthraquinone in concentrated sulfuric acid and subsequent precipitation with water and ice. After filtration and washing with water, the precipitated diazonium salt can either be dried under vacuum at low temperature or used direct in the still moist state.

The 2-methyleneglutaronitrile is used in stoichiometric amount or, preferably, in excess, based on 1-anthraquinone diazonium salt. It is especially advantageous to use a 1- to 10-fold molar excess, most preferably a 2- to 6-fold molar excess, of 2-methyleneglutaronitrile, based on the diazonium salt.

Suitable catalysts for the reaction of the 1-anthraquinone diazonium salt with 2-methyleneglutaronitrile are e.g. iron or copper powder, iron or copper salts, or mixtures or iron powder and iron salt or of copper powder and copper salt. The metal salts are preferably the corresponding chlorides. If a mixture of metal powder and metal salt is used as catalyst, then both are preferably employed in the ratio 1:1.

It is preferred to use a catalytic amount of copper powder or copper(I) or copper(II) chloride. The use of copper(I) chloride is most preferred.

The catalyst is used in an amount of e.g. 1 to 5% by weight, based on 1-anthraquinone diazonium salt.

Suitable solvents for the reaction of the 1-anthraquinone diazonium salt with 2-methyleneglutaronitrile are preferably polar solvents, e.g. $C_1$-$C_4$alkanols such as methanol, ethanol, n-propanol or isopropanol, or n-butanol or isobutanol; nitriles such as acetonitrile or isopentyl nitrile; ketones such as acetone; or phosphorus containing compounds such as dimethyl methanephosphonate. It is preferred to use $C_1$-$C_4$alkanols or phosphorus containing compounds, especially dimethyl methanephosphonate or, most preferably, methanol.

The reaction of the 1-anthraquinone diazonium salt with 2-methyleneglutaronitrile is conveniently carried out in the temperature range from 20° to 100° C.

The cyanhydrin of formula (3) can be converted into the ketonitrile of formula (4) in the temperature range from about 40° to 180° C., preferably from 70° to 150° C. A useful medium for this reaction consists of an inert solvent and an acid ion exchanger. Examples of suitable inert solvents are alkanols such as ethanol, n-propanol or isopropanol, n-butanol or isobutanol or, preferably, aromatic hydrocarbons such as toluene, xylene or chlorobenzene. Examples of suitable ion exchangers are strongly acid cationic ion exchangers and, among these, preferably synthetic resin derivatives, e.g. ion exchangers that contain sulfonic acid groups.

An alkaline medium consisting e.g. of a base and a solvent is used for the cyclisation. Examples of suitable bases are alkali metal hydroxides such as sodium hydroxide or potassium hydroxide, alcoholates such as sodium methanolate or potassium methanolate, or alkali metal carbonates such as sodium carbonate or potassium carbonate. Suitable solvents are e.g. polar aprotic solvents such as dimethylformamide, dimethylsulfoxide, hexamethylphosphoric triamide or glycol ethers, e.g. diethylene glycol diethyl ether or diethylene glycol dimethyl ether.

The cyclisation is carried out at a temperature up to 80° C., preferably in the range from 40° to 70° C. Surprisingly, in the course of this reaction not only is the ketonitrile (4) cyclised to the benzanthrone, but also a second cyclisation to give the lactone takes place.

The invention further relates to cyanhydrins of the above formula (3), wherein $R_1$, $R_2$ and $R_3$ have the meanings and preferred meanings assigned to them previously.

The invention further relates to compounds of formula

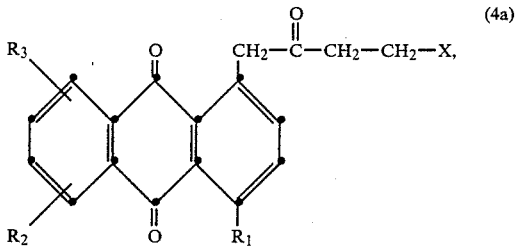

wherein $R_1$, $R_2$ and $R_3$ have the meanings and preferred meanings assigned to them previously and X is —CN or —COOH. Compounds of formula (4a), wherein X is —COOH, can be readily obtained from the analogous compounds of formula (4), e.g. by acid saponification of the cyano group in a manner known per se.

The compounds of formulae (3) and (4a) are useful intermediates for the synthesis of a large number of substituted anthraquinones and heterocycles.

With primary, secondary or tertiary amines, especially with high boiling amines having a boiling point of ≧150° C., e.g. dibutylamine, diisobutylamine, tripropylamine, tetramethylbutylamine, N,N-dimethylaniline or N,N-diethylaniline, the benzanthrone lactones of formula (1) give deep blue dyeings.

In addition, the benzanthrone lactones of this invention are useful coupling components for the synthesis of novel hydrazono dyes.

Accordingly, in yet another of its aspects the present invention relates to dyes of formula

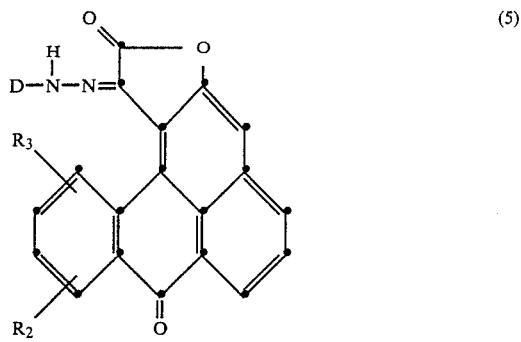

and tautomers thereof, wherein $R_1$, $R_2$ and $R_3$ are as previously defined and D is the radical of a diazo component. In this connection, $R_1$, $R_2$ and $R_3$ have the preferred meanings assigned to them previously.

The diazo radical D is derived e.g. from an aromatic carbocyclic or heterocyclic amine of the general formula

D—NH$_2$.

Preferably this amine is an aminobenzene or a mono- or bicyclic compound which contains an aromatic-heterocyclic 5- or 6-membered ring.

The aminobenzene and the heterocyclic amine can carry one or more additional substituents, e.g. $C_1$–$C_4$alkyl such as methyl, ethyl, n-propyl or isopropyl, or n-butyl, sec-butyl or tert-butyl, $C_1$–$C_4$alkoxy, preferably methoxy, halogen such as bromine and, preferably, chlorine, or nitro, cyano, sulfo, carbalkoxy such as carbomethoxy or carbethoxy, alkylsulfonyl such as methylsulfonyl, or unsubstituted, mono- or dialkylated or arylated sulfonamide such as N-methylsulfonamide, N-phenylsulfonamide or N,N-dimethylsulfonamide.

If the amine is a heterocyclic amine, the basic heterocycle may be e.g. a thiazole, benzthiazole, benzisothiazole, pyridine, quinoline, pyrazole, thiophene or phthalimide.

Examples of suitable heterocyclic amines are: 2-aminothiazole, 2-amino-5-nitrothiazole, 3-aminobenzisothiazole, 3-aminopyridine, 3-aminoquinoline, 2-amino-6-methylbenzthiazole, 2-amino-4-cyanopyrazole, 3- or 4-aminophthalimide.

The diazo radical is preferably derived from an aminobenzene. The aminobenzene is most preferably unsubstituted or is further substituted by methoxy, chlorine, nitro, cyano and/or methyl.

Examples of suitable aminobenzenes are: aniline, 1-amino-4-chlorobenzene, 1-amino-2-cyano-4-chlorobenzene, 1-amino-2-carbomethoxy-4-chlorobenzene, 4-nitroaniline, sulfanilic acid, 4-methoxyaniline, 3,5-dinitroaniline, 1-aminobenzene-2-, -3- or -4-sulfonamide, 1-amino-4-methylsulfonylbenzene, 1-amino-2,4-dicyanobenzene, 1-amino-2-cyano-4-nitrobenzene, 4-chloro-2-nitroaniline.

The novel hydrazono dyes of formula (5) can be prepared in a manner known per se, e.g. by diazotising a diazo component of formula

D—NH₂ and coupling the diazonium salt to a benzanthrone lactone of formula (1).

The novel compounds or mixtures thereof are suitable for dyeing and printing e.g. leather, wool, silk, and synthetic fibres, for example acrylic or acrylonitrile fibres, polyacrylonitrile fibres and copolymers of acrylonitrile and other vinyl compounds, e.g. acrylic ester, acrylamide, vinyl pyridine, vinyl chloride or vinylidene chloride, copolymers of dicyanoethylene and vinyl acetate, and acrylonitrile block copolymers, polyurethane and polyolefin fibres such as basically modified polypropylene, polypropylene modified with nickel, or unmodified polypropylene, cellulose triacetate and cellulose 2½ acetate, and polyamide fibres, e.g. nylon 6, nylon 6.6 or nylon 12, and aromatic polyester fibres, e.g. those obtained from terephthalic acid and ethylene glycol.

A preferred utility of the novel dyes of formula (5), which do not contain water-solubilising groups, is that of dyeing synthetic fibre-forming polymers such as polyamides, polyolefins and, in particular, polyesters. The fibres can be dyed by e.g. conventional methods of dyeing polyester materials. Normally, strong red to orange dyeings or also prints of good fastness properties are obtained, in particular good fastness to heat setting, sublimation, pleating, exhaust gas, cross-dyeing, dry cleaning and chlorine, and good wetfastness properties such as fastness to water, washing and perspiration.

In the following Examples parts are by weight.

EXAMPLE 1

250 parts of 1-aminoanthraquinone are added at 50° C. over 1 hour to a solution of 85 parts of sodium nitrite in 750 ml of concentrated H₂SO₄. The reaction mixture is then stirred for half an hour at this temperature and poured on to ice. The diazonium salt is filtered with suction and washed with ice water.

The diazonium salt is pressed as dry as possible and then suspended in a mixture of 2000 ml of methanol and 530 parts of 2-methyleneglutaronitrile and the suspension is heated to 40° C. Then 4 parts of copper(I) chloride are added in small portions over 15 minutes. When the evolution of nitrogen has ceased, the temperature is raised to 50°-55° C. and kept for 1½ hours. The reaction solution is then cooled to about 10° C. and 37.5 parts of anthraquinone are filtered from the solution. The filtrate is concentrated and 282 parts of crude product are isolated by filtration and subsequently extracted in a soxhlett with cyclohexane, affording 267 parts of 3-hydroxy-4-(1-anthraquinone)-1,3-butanedicarbonitrile. Melting point: 144°-146° C.

EXAMPLE 2

8 parts of 3-hydroxy-4-(1-anthraquionone)-1,3-butanedicarbonitrile obtained in Example 1 and 0.8 part of neutral aluminium oxide are suspended in 50 ml of xylene and the suspension is refluxed for 40 minutes. After the addition of activated charcoal, the reaction solution is filtered hot and the filtrate is evaporated to dryness. Recrystallisation of the residue yields 5.9 g of 3-oxo-4-(1-anthraquinone)-butanecarbonitrile. Melting point: 165°-167° C.

EXAMPLE 3

5 parts of 3-oxo-4-(1-anthraquinone)-butanecarbonitrile obtained in Example 2 are stirred for 2 hours in 40 ml of concentrated sulfuric acid. The reaction solution is then poured slowly into 200 parts of ice water and stirring is continued for 12 hours. The solid is filtered with suction and washed, affording 5.1 parts of 3-oxo-4-(1-anthraquinone)butyric acid. Melting point after recrystallisation: 195° C.

EXAMPLE 4

To a stirred solution of 16.5 parts of 3-oxo-4-(1-anthraquinone)-butanecarbonitrile obtained in Example 2 and 100 ml of dimethylformamide are added 13.5 parts of sodium methanolate such that the temperature does not exceed 50° C. Stirring is continued for 45 minutes, then the suspension is cooled and added to a solution of 50 ml of concentrated hydrochloric acid and 600 ml of H₂O. The precipitated solid is filtered with suction, washed and dried, affording 13 parts of 1H-anthra[1,9-ef]benzo[b]furan-2,8-dione of formula

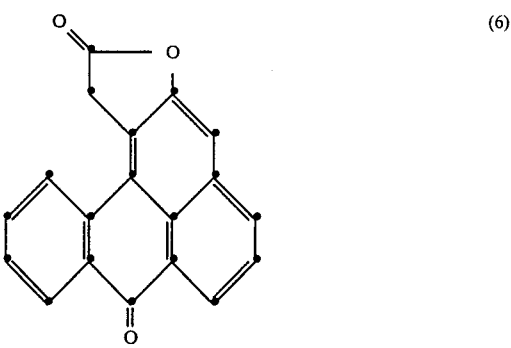

(6)

Melting point after recrystallisation: 300° C. (dec).

EXAMPLE 5

An aqueous solution of 1.7 parts of 4-methoxyphenyl diazonium chloride is added to a slurry of 2 parts of 1H-anthra[1,9-ef]benzo[b]furan-2,8-dione in 100 ml of dimethylformamide and the batch is stirred for 24 hours. The precipitated solid is then filtered with suction and washed with dimethylformamide and methanol, affording 2.7 parts of 1-(4-methoxyphenylhydrazono)anthra[1,9-ef]benzo[b]furan-2,8-dione of formula

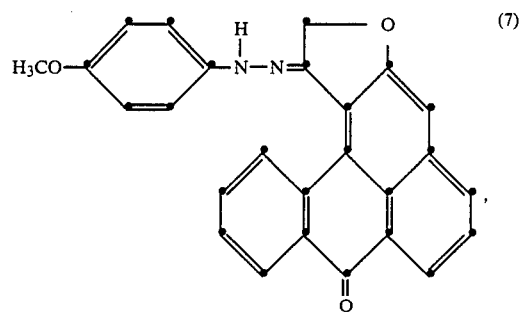

(7)

which dyes polyester fibres in a red shade of good fastness properties.

EXAMPLE 6-10

Following the procedure described in Example 5, but using diazonium salts which are derived from the amines listed in the table instead of 4-methoxyphenyl diazonium chloride, analogous dyes which dye polyester fibres in red to orange shades are obtained:

| Example | Diazocomponent | $\lambda_{max}$ [nm] |
|---|---|---|
| 6 | aniline | 482 |
| 7 | 4-chloroaniline | 482 |
| 8 | 4-nitroaniline | 504 |
| 9 | 3,5-dinitroaniline | 461 |
| 10 | sulfanilic acid | 493 |

What is claimed is:

1. A benzanthrone lactone of formula

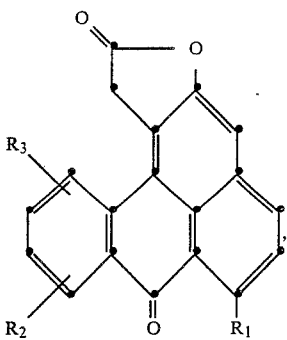
(1)

wherein $R_1$ is hydrogen or hydroxy and $R_2$ and $R_3$ are each independently of the other hydrogen, chlorine, hydroxy, methoxy or benzamido.

2. A benzanthrone lactone according to claim 1, wherein $R_1$ is hydrogen.

3. A benzanthrone lactone according to claim 1, wherein $R_2$ and $R_3$ are each independently of the other hydrogen, chlorine or benzamido.

4. A benzanthrone lactone according to claim 1, wherein $R_2$ and $R_3$ are hydrogen.

5. A benzanthrone lactone according to claim 1, wherein $R_1$, $R_2$ and $R_3$ are each hydrogen.

* * * * *